US009808184B2

United States Patent
Sakai et al.

(10) Patent No.: US 9,808,184 B2
(45) Date of Patent: Nov. 7, 2017

(54) MOTOR FUNCTION EVALUATION DEVICE AND MOTOR FUNCTION EVALUATION METHOD

(71) Applicant: TANITA CORPORATION, Tokyo (JP)

(72) Inventors: Yoshio Sakai, Tokyo (JP); Tomoko Takehara, Tokyo (JP); Tomohiro Okura, Ibaraki (JP); Taishi Tsuji, Ibaraki (JP)

(73) Assignee: TANITA CORPORATION, Tokyo (JP)

( * ) Notice: Subject to any disclaimer, the term of this patent is extended or adjusted under 35 U.S.C. 154(b) by 103 days.

(21) Appl. No.: 14/058,027

(22) Filed: Oct. 18, 2013

(65) Prior Publication Data
US 2014/0272853 A1  Sep. 18, 2014

Related U.S. Application Data

(60) Provisional application No. 61/784,897, filed on Mar. 14, 2013.

(51) Int. Cl.
*A61B 5/11* (2006.01)
*A61B 5/103* (2006.01)
(Continued)

(52) U.S. Cl.
CPC ............. *A61B 5/11* (2013.01); *A61B 5/1036* (2013.01); *A61B 5/1117* (2013.01);
(Continued)

(58) Field of Classification Search
CPC .................................................. A63B 5/0537
(Continued)

(56) References Cited

U.S. PATENT DOCUMENTS 4,091,449 A * 5/1978 Meckstroth .......... G01G 19/415
  177/25.15
4,831,527 A * 5/1989 Clark .................... A61B 5/1075
  600/553
(Continued)

FOREIGN PATENT DOCUMENTS

CN   102088902 A   6/2011
GB   2 422 790 A   8/2006
(Continued)

OTHER PUBLICATIONS

Extended European Search Report issued in European Application No. 13005116.2-1506 dated Jun. 16, 2014.
(Continued)

*Primary Examiner* — Xuan Thai
*Assistant Examiner* — Sadaruz Zaman
(74) *Attorney, Agent, or Firm* — McDermott Will & Emery LLP

(57) ABSTRACT

To provide a motor function evaluation device and a motor function evaluation method capable of evaluating a motor function of a subject comprehensively and easily. A motor function evaluation device 1 of the present invention includes a measurement base 11, a load measurement unit 14 that measures load change over time of the subject applied to the measurement base 11, and an arithmetic unit 24 that determines a balance ability indicator of the subject determined by the load change over time measured by the load measurement unit 14. The arithmetic unit 24 determines the balance ability indicator from a time interval from when the subject stands up and the load applied to the load measurement unit 14 is maximized until when the load variation is stabilized.

6 Claims, 10 Drawing Sheets

(51) Int. Cl.
*A61B 5/00* (2006.01)
*G01G 19/50* (2006.01)
*A61B 5/22* (2006.01)

(52) U.S. Cl.
CPC .......... *A61B 5/4023* (2013.01); *A61B 5/7275* (2013.01); *G01G 19/50* (2013.01); *A61B 5/224* (2013.01); *A61B 5/743* (2013.01)

(58) Field of Classification Search
USPC ................................................ 434/247, 258
See application file for complete search history.

(56) References Cited

U.S. PATENT DOCUMENTS

| | | | | |
|---|---|---|---|---|
| 5,280,429 | A * | 1/1994 | Withers | A61B 5/0535 378/70 |
| 6,294,891 | B1 * | 9/2001 | McConnell | G05B 5/01 318/560 |
| 6,782,340 | B1 * | 8/2004 | Komatsu | A61B 5/0537 177/246 |
| 7,163,516 | B1 | 1/2007 | Pagnacco et al. | |
| 8,961,185 | B2 * | 2/2015 | Bleich | A61B 5/0456 434/247 |
| 2001/0053883 | A1 * | 12/2001 | Yoshimura | A61B 5/0537 600/587 |
| 2003/0088197 | A1 | 5/2003 | Itagaki | |
| 2006/0179938 | A1 * | 8/2006 | Kawai | A61B 5/22 73/379.01 |
| 2008/0059097 | A1 | 3/2008 | Sakai | |
| 2008/0071186 | A1 * | 3/2008 | Kasahara | A61B 5/0537 600/547 |
| 2008/0188775 | A1 * | 8/2008 | Schneider | G01G 19/50 600/592 |
| 2013/0040272 | A1 * | 2/2013 | Booher | A63B 24/0075 434/254 |
| 2013/0041235 | A1 * | 2/2013 | Rogers | A61B 5/6867 600/306 |
| 2014/0272853 | A1 * | 9/2014 | Sakai | A61B 5/1036 434/247 |

FOREIGN PATENT DOCUMENTS

| | | |
|---|---|---|
| JP | 2006-51158 A | 2/2006 |
| JP | 2008-092979 A | 4/2008 |
| JP | 2011-045480 A | 3/2011 |
| WO | 2009/093632 A1 | 7/2009 |

OTHER PUBLICATIONS

Extended European Search Report issued in European Application N. 13005116.2 dated Oct. 8, 2014.
Chinese Office Action dated Aug. 11, 2015, issued in corresponding Chinese Application No. 201310723570.9.

\* cited by examiner

```
MF MOTOR FUNCTION AGE 60 POINTS
108 TH/251 PERSONS
```

```
MF MOTOR FUNCTION AGE 58 POINTS
39 TH/86 PERSONS IN THEIR 60S
```

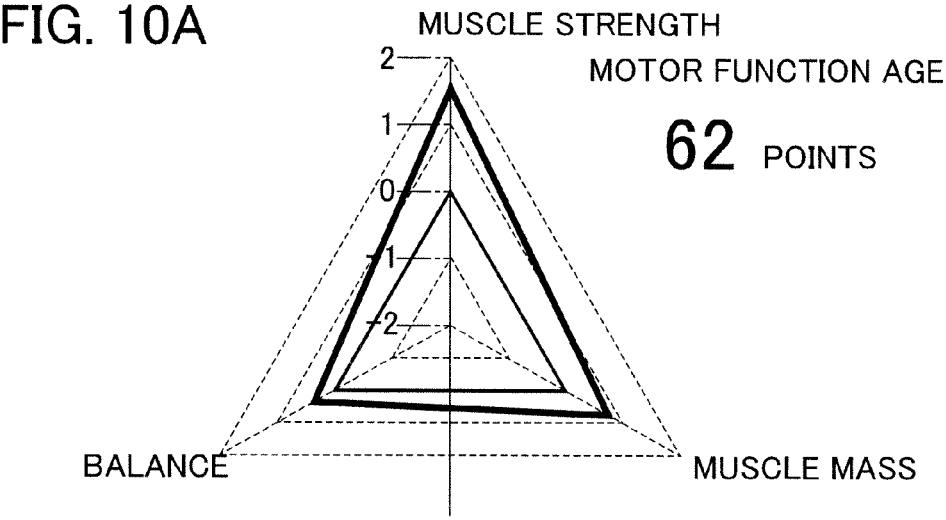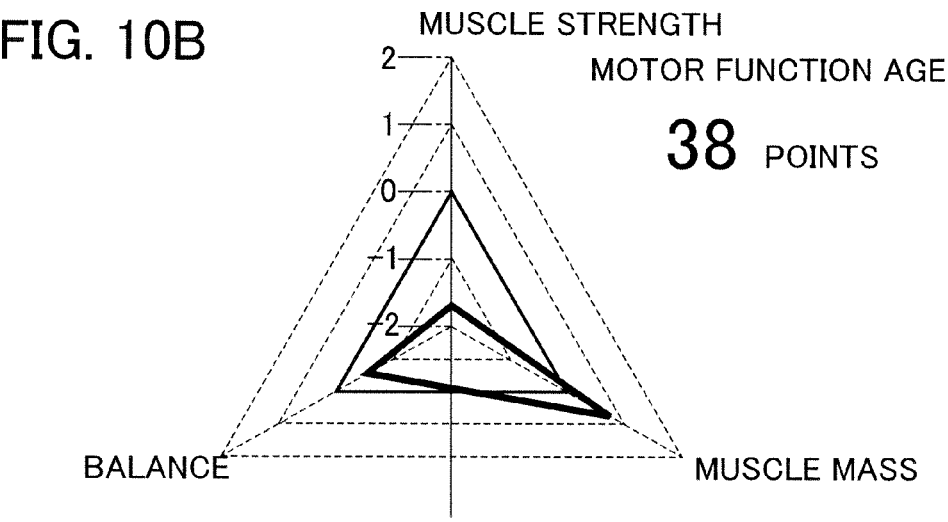

MOTOR FUNCTION EVALUATION DEVICE AND MOTOR FUNCTION EVALUATION METHOD

This application is based on and claims the benefit of priority from U.S. Provisional Patent Application No. 61/784,897, filed on 14 Mar. 2013, the content of which is incorporated herein by reference.

BACKGROUND OF THE INVENTION

Field of the Invention

The present invention relates to a motor function evaluation device and a motor function evaluation method.

Related Art

Conventionally, replies to questionnaire surveys and results of physical performance tests have been used to evaluate motor functions.

However, criteria for judging the questionnaire surveys are not clear, and hence evaluation results are less objective.

Further, the physical performance tests are performed on a large scale as different kinds of equipment, time and space are required to carry out various test items. With the physical performance tests, there are risks of injuries due to falling and the like even though considerations are given to safety, especially when a subject is the elderly. Further, professional judgment and advice in a comprehensive manner are required in order to judge test results of the respective items. Furthermore, it is considered to be important to capture changes over time in the motor function evaluation. However, due to the large scale of the physical performance tests as described above, it is difficult to perform the physical performance tests many times.

In view of the above, there is an evaluation device of lower-limb muscle strength that measures the body weight of a subject on a measurement base, and measures the lower-limb muscle strength of the subject based on a maximum peak and a minimum peak of a load applied to the measurement base when the subject changes his or her posture from a crouching posture to a standing posture on the measurement base (refer to Patent Document 1).

[Patent Document 1] Japanese Unexamined Patent Application, Publication No. 2008-92979

SUMMARY OF THE INVENTION

However, the evaluation device of the lower-limb muscle strength according to the Patent Document 1 evaluates the lower-limb muscle strength only.

It is an object of the present invention to provide a motor function evaluation device and a motor function evaluation method capable of evaluating a motor function of a subject comprehensively and easily.

The present invention is made to achieve the object by the following means. It should be noted that, in order to facilitate understanding, the numerals corresponding to the embodiment of the present invention are added for explanation, but this is not restrictive. Components to be explained with the numerals may be modified as appropriate, and may be at least partially substituted by other components.

A first aspect of the present invention provides a motor function evaluation device (1) including a measurement base (11), a load measurement unit (14) that measures load change over time of a subject applied to the measurement base (11), and an arithmetic unit (24) that determines a balance ability indicator of the subject determined by the load change over time measured by the load measurement unit (14) in which the arithmetic unit (24) determines the balance ability indicator from a time interval from when the subject stands up and the load applied to the load measurement unit (14) is maximized until when variation of the load is stabilized.

A second aspect of the present invention provides the motor function evaluation device (1) of the first aspect of the present invention, in which the time when the load is stabilized is defined as a time after a lapse of two cycles or a time having the same value as the body weight value after the lapse of the two cycles, after when the load applied to the load measurement unit (14) is maximized.

A third aspect of the present invention provides a motor function evaluation device (1) including a measurement base (11), a load measurement unit (14) that measures load change over time of a subject applied to the measurement base (11), an arithmetic unit (24) that determines two or more motor function indicators including at least one of a muscle strength indicator of the subject or a balance ability indicator of the subject determined by the load change over time measured by the load measurement unit (14), and an evaluation unit (24) that evaluates a motor function of the subject by using the two or more motor function indicators determined by the arithmetic unit (24).

A fourth aspect of the present invention provides the motor function evaluation device (1) of the third aspect of the present invention further including an impedance measurement unit (15) that determines a biological impedance of the subject on the measurement base (11) in which the arithmetic unit (24) determines two or more motor function indicators out of the muscle strength indicator, the balance ability indicator, and a muscle mass indicator that is obtained by an arithmetic computation based on the biological impedance determined by the impedance measurement unit (15).

A fifth aspect of the present invention provides the motor function evaluation device (1) of the third or fourth aspect of the present invention, in which the arithmetic unit (24) determines the balance ability indicator from a time from when the subject stands up and the load applied to the load measurement unit (14) is maximized until when variation of the load is stabilized.

A sixth aspect of the present invention provides the motor function evaluation device (1) of the fifth aspect of the present invention, in which the time when the variation of the load is stabilized is defined as a time after a lapse of two cycles or a time having the same value as the body weight value after the lapse of the two cycles, after when the load applied to the load measurement unit (14) is maximized.

A seventh aspect of the present invention provides the motor function evaluation device (1) according to any one of the third to the sixth aspects of the present invention, in which the arithmetic unit (24) determines the muscle strength indicator and the balance ability indicator from variation of the load over time measured by the load measurement unit (14) when the subject stands up onto the measurement base (11).

An eighth aspect of the present invention provides the motor function evaluation device (1) according to any one of the third to the seventh aspects of the present invention, in which the arithmetic unit (24) determines the muscle strength indicator and the balance ability indicator from variation of the load over time measured by the load measurement unit (14) when the subject stands up from a chair onto the measurement base (11).

A ninth aspect of the present invention provides the motor function evaluation device (1) according to any one of the third to the eighth aspects of the present invention, in which the arithmetic unit (24) determines the muscle strength indicator from a value that is obtained by dividing a maximum value of the load measured by the load measurement unit (14) by a body weight of the subject.

A tenth aspect of the present invention provides a motor function evaluation method including the steps of measuring load change over time of a subject applied to a measurement base (11), determining two or more motor function indicators including at least one of a muscle strength indicator showing muscle strength of the subject or a balance ability indicator showing balance ability of the subject determined by information showing the measured load change over time, and evaluating a motor function of the subject by using the two or more motor function indicators.

The following effects can be obtained by the present invention.

According to the first aspect of the present invention, the motor function of the subject can be evaluated by using the balance ability indicator. According to the balance ability indicator, the motor function can be measured by an easy standing up motion, and therefore, risks of injuries due to falling and the like can be reduced especially when the subject is the elderly.

Further, the motor function evaluation can be made by the standing up motion, which can be performed conveniently and easily.

The motor function indicator is determined by the load change over time of the subject that is measured by the load measurement unit, which is objective as compared with the motor function evaluation by the questionnaire survey, the physical performance tests and the like. Further, the motor function evaluation can be made without using different kinds of equipment, time, space and the like.

According to the second aspect of the present invention, it is possible to choose an optimum time as the time until when the load variation is stabilized, as the stagger of the subject, who is standing up onto the load measurement unit, has the two cycles after when the load applied to the load measurement unit is maximized, in most cases. Thus, the balance ability indicator can be determined accurately.

According to the third aspect of the present invention, the motor function of the subject can be evaluated in a comprehensive manner by using the two or more motor function indicators. The motor function indicators are determined by the load change over time of the subject that is measured by the load measurement unit, which is objective as compared with the motor function evaluation by the questionnaire survey, the physical performance tests and the like. Further, the comprehensive motor function evaluation can be made by one motor function evaluation device, without using the different kinds of equipment, time, space and the like.

According to the fourth aspect of the present invention, the muscle mass indicator by the biological impedance can also be added to the comprehensive motor function evaluation.

According to the fifth aspect of the present invention, a burden is further reduced as the subject stands up from the chair, in addition to the effect of the third aspect of the present invention.

According to the sixth aspect of the present invention, it is possible to choose the optimum time as the time until when the load variation is stabilized, as the stagger of the subject, who is standing up onto the load measurement unit, has the two cycles after when the load applied to the load measurement unit is maximized, in most cases. Thus, the balance ability indicator can be determined accurately.

According to the seventh aspect of the present invention, the motor function can be measured by the easy standing up motion from the measurement base. Therefore, the risks of injuries due to the falling and the like can be reduced especially when the subject is the elderly. Further, the motor function evaluation can be made comprehensively by the standing up motion from the measurement base, which can be performed conveniently and easily.

According to the eighth aspect of the present invention, the muscle strength indicator is determined from a value obtained by dividing a maximum value of the load that is measured by the load measurement unit by a body weight of the subject. The muscle strength indicator that is determined by a maximum value to body weight ratio F/Wt has higher accuracy than a muscle strength indicator that is determined by F/Wt obtained by dividing a difference ΔF between the maximum value and a minimum value by the body weight.

According to the ninth aspect of the present invention, the balance ability indicator is determined from the time from when the subject stands up and the load applied to the load measurement unit is maximized until when the load variation is stabilized. Thus, it is possible to evaluate the balance during the standing up motion (under the load) in a natural motion.

BRIEF DESCRIPTION OF THE DRAWINGS

FIG. 9A shows other examples of displaying an overall motor function indicator MF that is determined as above, in which FIG. 9A ranking in the total is showing, FIG. 9B shows other examples of displaying an overall motor function indicator MF that is determined as above, in which ranking by age is shown;

FIG. 10A shows examples of modifications of displaying the overall motor function indicator MF, and FIG. 10B shows examples of modifications of displaying the overall motor function indicator MF.

EXPLANATION OF REFERENCE NUMERALS

1: motor function evaluation device, 10: measurement unit, 11: measurement base, 12: load sensors, 13: electrodes, 14: load measurement circuit (load measurement unit), 15: impedance measurement circuit (impedance measurement unit), 20: display screen, 20: display unit, 21: display screen, 22: output port, 23: operating switches, 24: CPU (arithmetic unit, evaluation unit), 30: chair

DETAILED DESCRIPTION OF THE INVENTION

Figure 1:
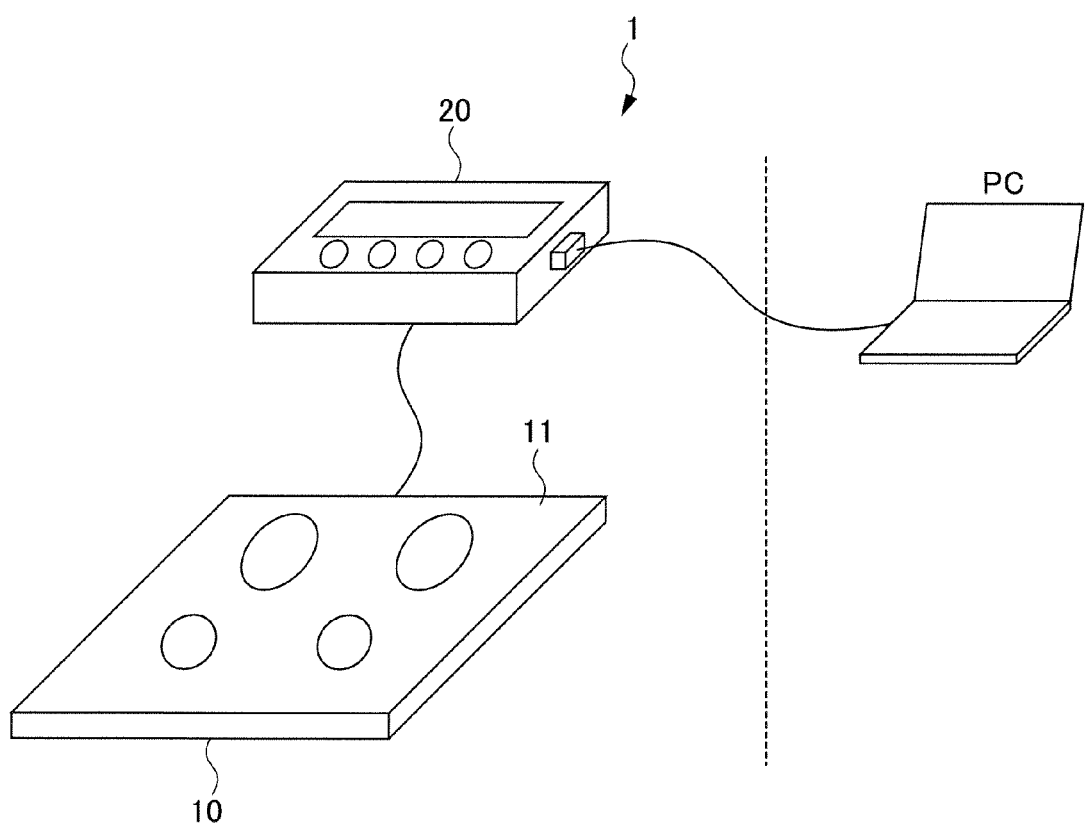
FIG. 1 is a view showing the appearance of a motor function evaluation device according to an embodiment of the present invention.
Figure 2:
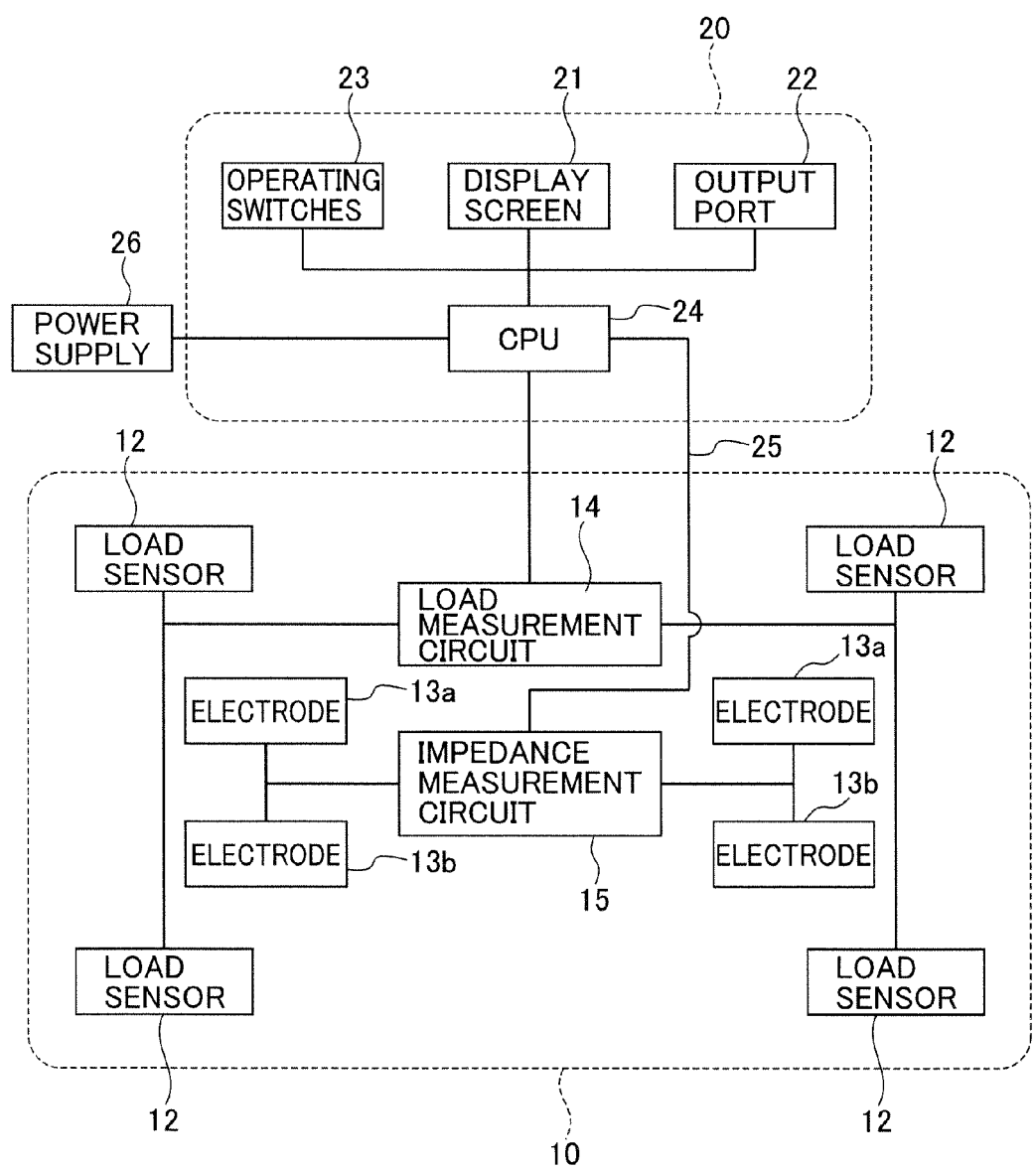
FIG. 2 is a block diagram showing the inside of the motor function evaluation device.

Hereinafter, a motor function evaluation device 1 according to an embodiment of the present invention will be explained with reference to the accompanying drawings. FIG. 1 is a view showing the appearance of the motor function evaluation device 1 according to the embodiment of the present invention. FIG. 2 is a block diagram showing the inside of the motor function evaluation device 1.

As shown in FIG. 1, the motor function evaluation device 1 includes a measurement unit 10 and a display unit 20.

The measurement unit 10 has a horizontal measurement base 11 to be stepped on by a subject. As shown in FIG. 2, the measurement unit 10 includes in its inside load sensors 12 for performing load measurement, electrodes 13 (13a and 13b) for performing biological impedance measurement, a load measurement circuit 14, and an impedance measurement circuit 15.

Each of the load sensors 12 is formed by a load cell or the like, and is arranged at four corners of the rectangular measurement base 11.

Although detailed illustration is omitted, each of the load sensors 12 includes a strain body that is deformed in response to an inputted load, and a strain gage that is pasted onto the strain body and outputs an electric signal (detection signal) having a value corresponding to the deformation of the strain body. It is preferable to provide three or more load sensors 12 in order to perform gravity center fluctuation measurement, and four load sensors 12 are contained according to this embodiment.

Each of the load sensors 12 generates and outputs the detection signal corresponding to the load acting perpendicularly on an area where the load sensor 12 is provided.

The respective load sensors 12 are connected to the load measurement circuit 14. When the subject steps onto the measurement base 11 of the measurement unit 10, the load applied to the measurement base 11 is detected by the respective load sensors 12. The respective load sensors 12 output the detection signals corresponding to the load to the load measurement circuit 14. Based on the detection signals outputted from the respective load sensors 12, the load measurement circuit 14 recognizes load values detected by the respective load sensors 12.

The four electrodes 13, each having a thin-plate shape, are arranged on the measurement base 11 with spaces therebetween. According to this embodiment, two electrodes 13a out of the four electrodes 13 are current-carrying electrodes, and the remaining two electrodes 13b are measuring electrodes.

The impedance measurement circuit 15 is able to supply a predetermined weak electrical current to the current-carrying electrodes 13a, and to measure a voltage across the measuring electrodes 13b. Based on current values applied by the current-carrying electrodes 13a and a voltage value measured across the measuring electrodes 13b, the impedance measurement circuit 15 is able to calculate a biological impedance of a person to be measured. Based on measurement results of the biological impedance of the subject, biological information such as body fat is derived.

The display unit 20 is connected to the measurement unit 10 via a cable, as shown in the drawing. However, this is not restrictive, and the display unit 20 may be attached to the top of a post that is attached onto the measurement unit 10, or the display unit and the measurement unit may be connected wirelessly, or may be formed integrally.

The display unit 20 includes a display screen 21 that displays the measurement results, a plurality of operating switches 23, an output port 22, and a CPU 24. Power is supplied to the display unit 20 from an external power supply 26.

The CPU 24 is a control device that performs centralized control of the motor function evaluation device 1. The operating switches 23 and the display screen 21 are connected to the CPU 24. Further, the CPU 24 is connected to the load measurement circuit 14 and the impedance measurement circuit 15 in the measurement unit 10 via cables 25.

The CPU 24 performs motor function evaluation based on an output from the load measurement circuit 14, an output from the impedance measurement circuit 15, other information of the subject inputted via the operating switches 23 and the like, as will be described later.

The operating switches 23 are the switches used for turning on/off the motor function evaluation device 1, inputting the information of the subject, inputting start of the measurement, and the like.

The display screen 21 displays a command and data that are inputted by the operation of the subject, and overall motor function evaluation.

The output port 22 is able to transmit data and the like to an external PC, as shown in FIG. 1.

(Overall Flow of Motor Function Evaluation)

Next, the motor function evaluation in the motor function evaluation device 1 will be explained.

Figure 3A:
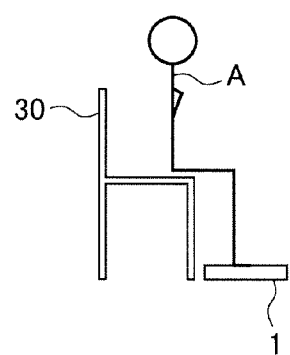
FIG. 3A is a view showing motions of a subject at the time of motor function evaluation.
Figure 3B:
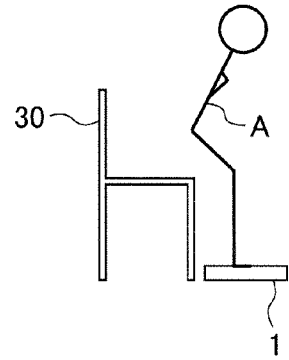
FIG. 3B is a view showing motions of a subject at the time of motor function evaluation.
Figure 3C:
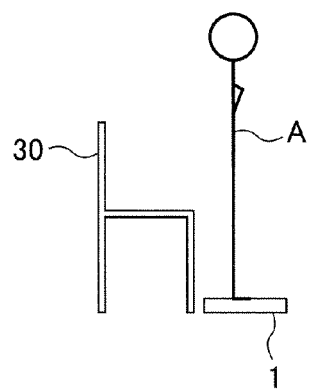
FIG. 3C is a view showing motions of a subject at the time of motor function evaluation.
Figure 4:
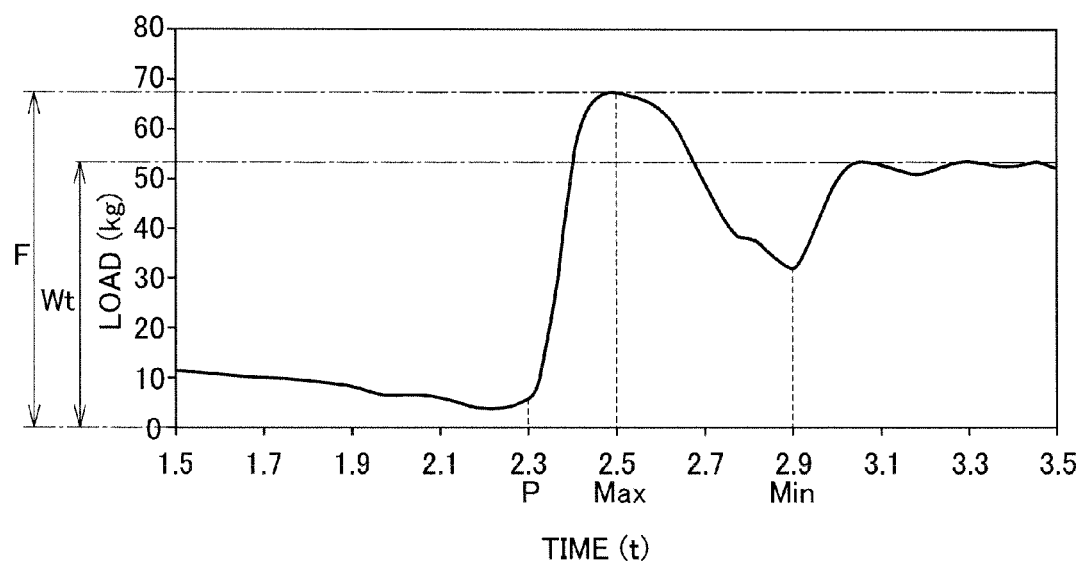
FIG. 4 is a graph showing load variation in a time series, corresponding to the motions of the subject as shown in FIG. 3.
Figure 4:
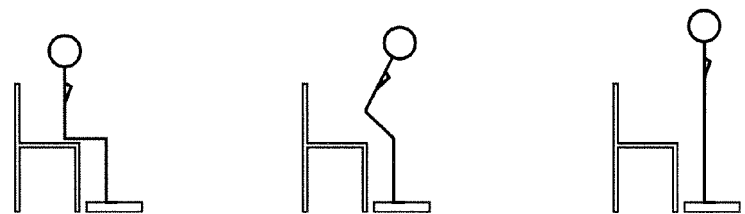

FIGS. 3A, 3B and 3C are views showing motions of a subject A at the time of the motor function evaluation. FIG. 4 is a graph showing load variation in a time series in the motor function evaluation device 1, corresponding to the motions of the subject A as shown in FIGS. 3A, 3B and 3C. The motions of the subject A during the measurement, as shown in FIGS. 3A, 3B and 3C, are shown under the graph of FIG. 4, in order to facilitate understanding.

As shown in FIGS. 3A, 3B and 3C, when performing the motor function evaluation in the motor function evaluation device 1, a chair 30 is first arranged next to the motor function evaluation device 1. The subject A sits down on the chair 30 while putting his or her feet on the measurement base 11 of the measurement unit 10 of the motor function evaluation device 1, as shown in FIG. 3A. Next, the subject A, who is sitting on the chair 30, stands up onto the motor function evaluation device 1, as shown in FIG. 3B. Then, the subject A waits until his or her body stops staggering and is stabilized, as shown in FIG. 3C.

During the above-described standing up motion of the subject A, the load measurement circuit 14 determines the load variation associated with the standing up motion of the subject A based on the detection signals from the load sensors 12, and outputs the load variation to the CPU 24.

Further, the electrodes 13 apply the weak electrical current to the subject A, and the impedance measurement circuit 15 measures the voltage across the electrodes 13a and 13b to determine the biological impedance of a living body, and outputs the biological impedance to the CPU 24.

When the subject A, who is sitting on the chair 30 while putting his or her feet on the measurement base 11, stands up, as shown in FIG. 4, the load is lightened at a position P in an early stage after the motion is started, and thereafter, a maximum load is recorded at a position Max. This is because the load is first shifted to the chair and buttocks, when the subject A tries to stand up from the chair.

After the position Max where a maximum load F is recorded, the load is reduced to be smaller than an actual body weight Wt of the subject A and a minimum load is recorded at a position Min that is smaller than the actual body weight Wt. Thereafter, the load goes up and down while its amplitude being damped, and the load is converged to the actual body weight Wt.

Based on the load variation and the measured biological impedance, the motor function evaluation device 1 is able to evaluate the motor function of the subject A including (1) muscle strength, (2) balance ability, and (3) muscle mass, as will be explained in detail later.

Incidentally, according to this embodiment, the motor function is evaluated based on the load variation by the standing up motion of the subject A who is sitting on the chair 30. However, this is not restrictive, and the subject A may stand up from a crouching state, without sitting on the chair 30.

It should be noted that, however, a heavy physical burden may be imposed on the subject A at the time of standing up from the crouching state, when the subject A is the elderly or has weak muscle strength. The burden is not so heavy when the subject A stands up from the chair 30, as described in this embodiment.

Further, the chair 30 is arranged next to the measurement unit 10 according to this embodiment. However, this is not restrictive, and the chair 30 may be arranged on the measurement unit 10 when there is enough space.

Hereinafter, the above-described (1) muscle strength, (2) balance ability, and (3) muscle mass will be explained for each in detail.

(1) Muscle Strength (1-1) Example of Muscle Strength Evaluation

The CPU 24 determines the maximum value F of the load from the measurement data of the load shown in FIG. 4 that is based on the load values transmitted from the load measurement circuit 14, and performs an arithmetic computation of a maximum value to body weight ratio F/Wt which is division of the maximum value F of the load by the actual body weight Wt of the subject. This F/Wt becomes an indicator of the muscle strength.

According to this embodiment, the muscle strength indicator is thus determined by the CPU 24 from the maximum value to body weight ratio F/Wt. However, this is not restrictive, and the muscle strength indicator may be defined as ΔF/Wt which is division of a difference ΔF between the maximum value F of the load and a minimum value of the load by the body weight Wt.

It should be noted that, however, the muscle strength indicator determined from the maximum value to body weight ratio F/Wt, as in this embodiment, has higher accuracy than the muscle strength indicator determined from ΔF/Wt.

This is because the difference ΔF between the maximum value F of the load and the minimum value of the load has low reliability and hence the ΔF/Wt also has low reliability, as it may be hard in the actual measurement to identify a point Min showing the minimum value, which is clearly shown in FIG. 4, when, for example, the subject A has the weak muscle strength.

Here, the point Max at which the load value shows the maximum value corresponds to the timing when the buttocks of the subject A get off the chair 30. It may also be hard to identify the maximum point Max in the actual measurement. Therefore, in this embodiment, a point having the maximum value, out of points at which the load equal to or greater than 105% of the body weight is recorded, after the detection of a point P at which the load fall to 20% or less of the body weight, is defined as the maximum point Max.

In the standing up motion from the state of sitting on the chair 30, the load is lightened in the early stage after the motion is started, and the maximum value is recorded after that. This is because the body weight is first shifted to the chair 30 and the buttocks when the subject A tries to stand up from the chair 30. Triggered by this, the maximum load point is detected.

Incidentally, the point P at which the load fall to 20% or less of the body weight may be a point at which the load is reduced by 30% (numerical value may be freely selected) of the body weight.

By identifying the maximum value by such a method using characteristics of the standing up motion of the subject A, it is possible to detect the maximum value point without fail.

(1-2) Modification of Muscle Strength Evaluation

The muscle strength indicator is not limited to the above-described maximum value to body weight ratio F/Wt, and a maximum increasing rate to body weight ratio (load change amount) RFD/Wt may be employed.

Figure 5A:
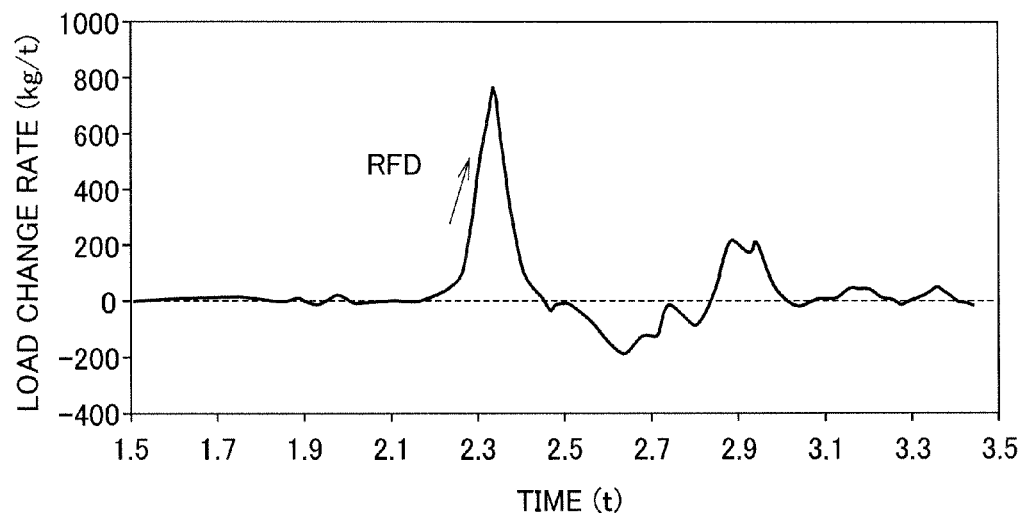
FIG. 5A is a graph showing a maximum increasing rate in a time series.
Figure 5B:
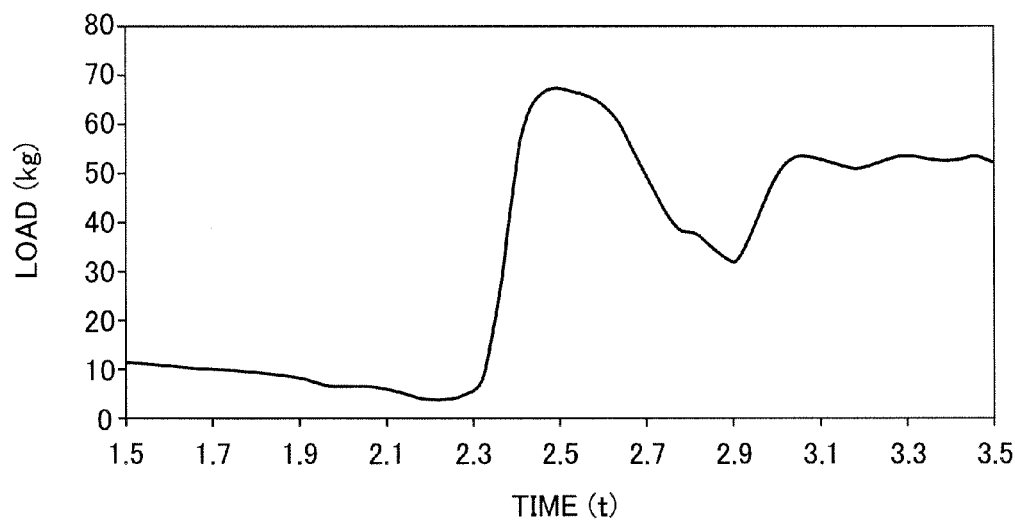
FIG. 5B is the same graph as FIG. 4 shown for comparison with FIG. 5A.

FIG. 5A is a graph showing the maximum increasing rate of the load in a time series. The same graph as FIG. 4 is shown as FIG. 5B for comparison to FIG. 5A in order to facilitate understanding. The maximum increasing rate RFD corresponds to inclination of a part having the steepest inclination in FIG. 5A.

Thus, the maximum increasing rate to body weight ratio RFD/Wt can also be employed as the muscle strength indicator.

(2) Balance Ability (2-1) Example of Balance Ability Evaluation

Figure 6:
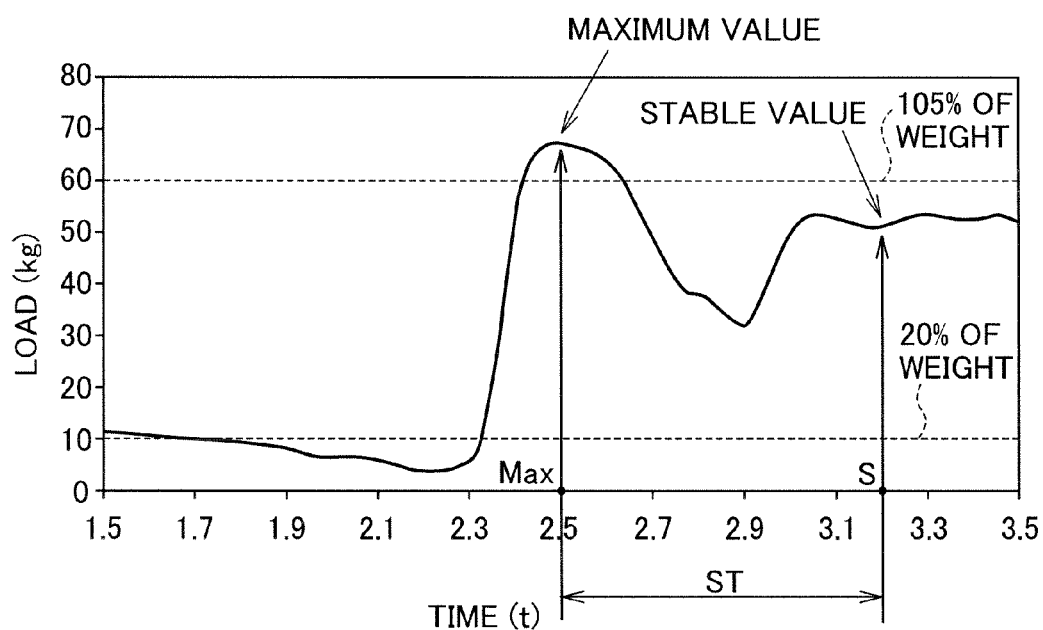
FIG. 6 is the same graph as FIG. 4, in which a maximum value, a stable value, and a time ST until a load is stabilized are described for valance ability measurement.
Figure 6:
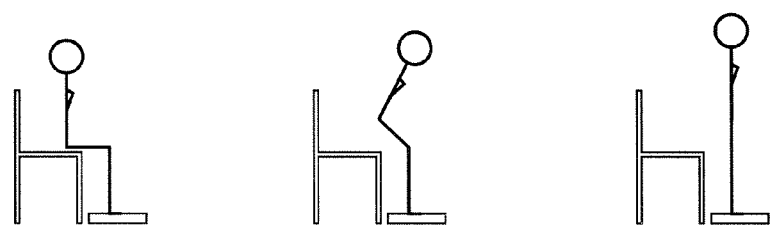

FIG. 6 is the same graph as FIG. 4, in which the maximum value of the load, a stable value, and a time ST until the load is stabilized are described, in order to explain balance ability evaluation.

According to the balance ability evaluation, the time ST from the point Max at which the load shows the maximum value until a point S at which the load is stabilized is measured, and the time ST is defined as a balance ability indicator.

When the subject A can stand up from the chair immediately, the ST becomes shorter. Meanwhile, when the subject A lacks horizontal balance, for example, the ST becomes longer.

By using the ST like this, it is possible to evaluate the balance during the standing up motion (under the load) in a natural motion.

In this embodiment, the time ST from the point Max at which the load shows the maximum value until the point S at which the load is stabilized is defined as the balance ability indicator. This is because the point Max showing the maximum value can be found more easily as compared with other points. However, this is not restrictive, and a time from when the load starts to rise until the point S at which the load is stabilized may be defined as the balance ability indicator.

Further, the point S at which the load is stabilized corresponds to the timing when the subject S is stabilized in a standing position, and when the load is near the body weight value.

Incidentally, the subject A may be regarded as being stabilized after the standing up motion on condition that the "variation in the load values falls within a certain range". However, when the subject A is the elderly, for example, and experiences a large stagger after standing up, a longer time is required before he or she is stabilized.

Figure 7A:
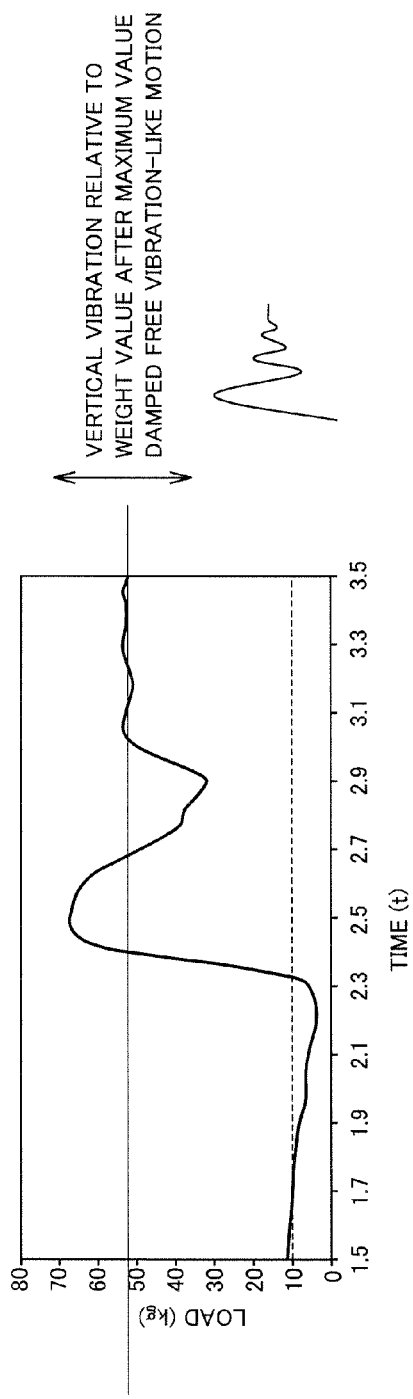
FIG. 7A is a graph explaining a stable point.
Figure 7B:
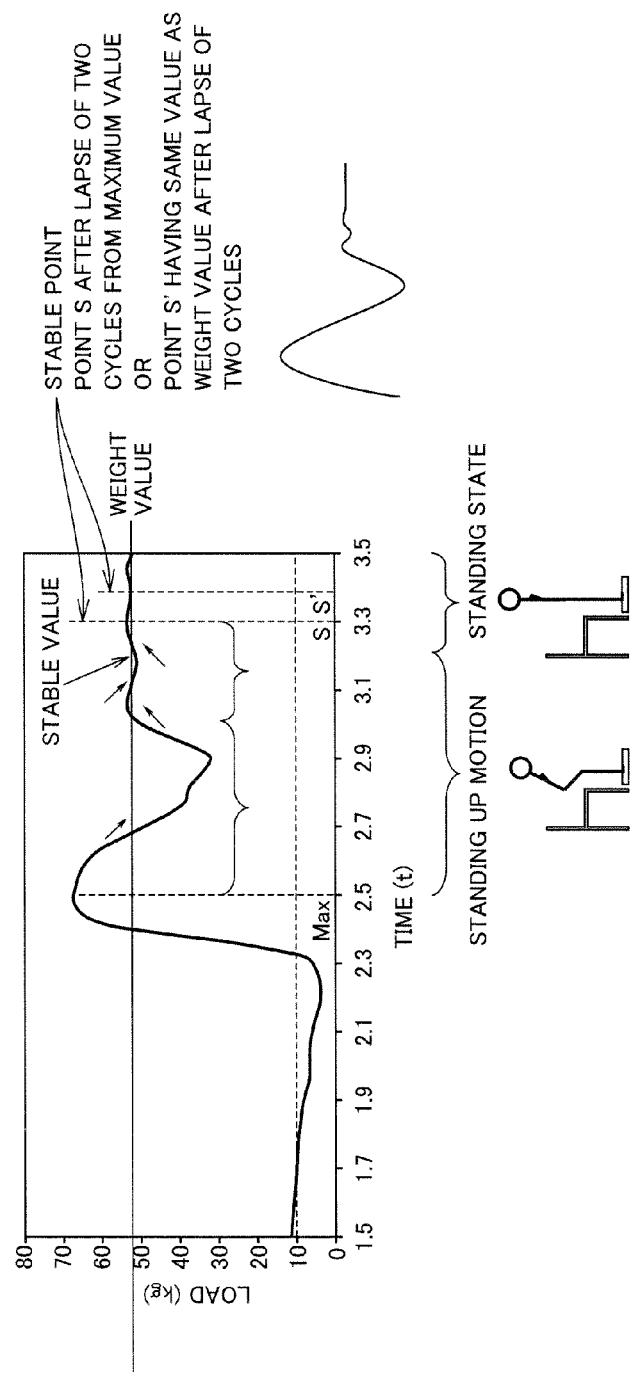
FIG. 7B is a graph explaining a stable point.

Therefore, in this embodiment, a point at which the load passes through the body weight value for the fourth time after the maximum value is detected is defined as a stable point. FIGS. 7A and 7B are views explaining such stable point S.

After standing up, a "stagger due to the standing up motion (quickness)" is followed by a "stagger in the standing state (gravity center fluctuation)". Therefore, the above two sections need to be divided in order to evaluate the balance in the standing up motion.

After the maximum value is detected (point Max) in the standing up motion, the load values of the load sensors 12 rebound to become smaller than the body weight. Thereafter, the load increases and decreases relative to the body weight Wt of the subject repeatedly for several times, before it is stabilized. That is, in the standing up motion, the load value after passing the maximum value shows a damped free vibration-like motion.

The staggers in the actual standing up motion include two cycles in most cases, as shown in FIG. 7B. Even in exceptional cases, the staggers include one or more, up to three, cycles.

Therefore, a time from when the maximum value of the "stagger due to the standing up motion (quickness)" is detected (point Max) until the point S at which the load is stabilized after the two cycles is defined as a stabilizing time ST. The following load increase and decrease relative to the body weight are defined as the "stagger in the standing state". Thus, the "stagger due to the standing up motion (quickness)" is separated from the "stagger in the standing state (gravity center fluctuation)".

The point S at which the load is stabilized after the two cycles is illustrated as the point S after a lapse of the two cycles from the maximum value. However, this is not restrictive, and a point S' that has the same value as the body weight after the lapse of the two cycles may be employed.

(2-2) Modification of Balance Ability Evaluation

In this embodiment, the ST value is defined as the balance ability indicator as explained above. However, this is not restrictive, and a locus length per time unit (L/T) as one of gravity center fluctuation indicators may be measured and employed as the balance ability indicator.

In this case, after the muscle strength is measured, the gravity center fluctuation measurement is performed after the stable point S (after being stabilized) to measure the locus length per time unit (L/T). Specifically, after the standing up motion, the gravity center fluctuation measurement is performed for a fixed period of time from the point S at which the load is stabilized, to determine a locus of the center of gravity. Then, a locus length is calculated and divided by the time, so as to obtain the locus length per time unit. The locus length per time unit is measured and calculated similarly to the general gravity center fluctuation measurement. Other gravity center fluctuation indicators, such as an area of the center of gravity (environmental, rectangular, and root mean square value) and horizontal balance, may be employed, instead of the locus length per time unit.

(3) Muscle Mass (3-1) Example of Muscle Mass Evaluation

After the gravity center fluctuation measurement, the motor function evaluation device 1 applies the electrical current to the electrodes 13, detects the voltage value across the electrodes by the impedance measurement circuit 15, and performs the arithmetic computation of the biological impedance value by the CPU 24, so as to determine leg muscle mass Lm.

According to this embodiment, the CPU 24 determines the leg muscle mass Lm according to the following expression.

$$Lm = a_1 \times \text{leg imp}/Ht^2 + b_1 \qquad \text{Expression (1)}$$

Incidentally, the leg muscle mass Lm may be determined according to the following expressions (2) and (3), instead of the expression (1).

$$Lm = \text{whole body muscle mass} - \text{arm muscle mass} - \text{trunk muscle mass} \qquad \text{Expression (2)}$$

$$Lm = c_1 \times \text{whole body imp}/Ht^2 - d_1 \times \text{arm imp}/Ht^2 - e_1 \times \text{trunk imp}/Ht^2 + f_1 \qquad \text{Expression (3)}$$

In the above-described expressions (1) to (3),
Lm is the leg muscle mass,
imp is the biological impedance,
Ht is the height (or may be the length of the respective regions), and
$a_1$, $b_1$, $c_1$, $d_1$, $e_1$, and $f_1$ are coefficients.

(Modification of Muscle Mass Evaluation)

In addition, "leg muscle mass/body weight" or "leg muscle mass/height$^2$" may be employed as an indicator for the muscle mass. Further, the muscle mass of the whole body and limbs may be employed, and the muscle mass may be standardized by the height or the body weight.

(4) Calculation of Overall Motor Function Indicator (4-1) Example of Calculation of Overall Motor Function Indicator Weights are assigned to the three indicators determined earlier by weighting factors $a_2$, $b_2$ and $c_2$ that are determined by multiple regression analysis, so as to calculate an overall motor function indicator MF based on the following expression.

$$MF = a_2 \times F/Wt + b_2 \times ST + c_2 \times Lm + d_2 \qquad \text{Expression (4)}$$

Where, MF is the motor function indicator,
F/Wt is the maximum value to body weight ratio (muscle strength indicator),
ST is the stabilizing time (balance indicator),
Lm is the leg muscle mass (muscle mass indicator), and
$a_2$, $b_2$, $c_2$ and $d_2$ are coefficients.

(Example of Display)

Figure 8A:
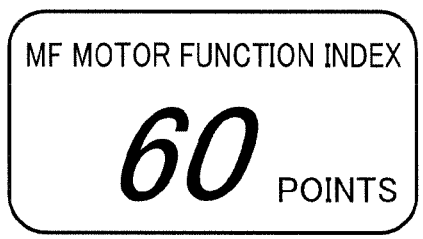
FIG. 8A is an example of displaying a deviation value relative to 50.
Figure 8B:
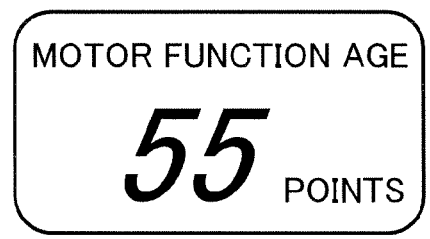
FIG. 8B is an example of displaying a motor function age.

FIGS. 8A and 8B show examples of displaying the overall motor function indicator MF that is determined as described above. FIG. 8A is an example of displaying the overall motor function indicator MF according to a deviation value relative to 50, and FIG. 8B is an example of expressing the overall motor function indicator MF according to a motor function age.

FIGS. 9A and 9B show other examples of displaying the overall motor function indicator MF that is determined as described above, and show comparison with others, that is, ranking of the obtained overall motor function indicator MF. Ranking obtained by the comparison with data measured by using the same device in the past, ranking among the persons to be measured of his or her age, or the like is displayed as the ranking. FIG. 9A shows the ranking in the total, and FIG. 9B shows the ranking by age.

By displaying the results with the ranking in this way, such effects can be expected as to notify the results in an easier to understand manner and to increase motivation to improve and maintain the motor function.

(Modification of Display)

Instead of displaying the determined overall motor function indicator MF as above, the respective indicators may be displayed separately. Further, from the measurement results, advice on weak points, how to exercise in order to overcome the weak points and the like may be displayed.

FIGS. 10A and 10B show examples of modifications of displaying the overall motor function indicator MF. When, for example, all of the muscle strength, the muscle mass, and the balance are higher than average values, as shown in FIG. 10A, such comments as "You have high muscle strength, relatively large amount of muscle mass, and nice balance. Risk of falling is low. Exercise appropriately to keep this state." may be displayed.

Further, when the muscle mass is above average but the muscle strength and the balance are lower than the average values, as shown in FIG. 10B, such comments as "You have relatively large amount of muscle mass, but low muscle strength and slightly unfavorable balance. There is risk of falling. Daily exercise to improve muscle strength is recommended." may be displayed.

(4-2) Modification of Calculation of Overall Motor Function Indicator

According to the above-described explanation, the overall motor function indicator MF is calculated from the three indicators of the muscle strength, the balance, and the muscle mass. However, this is not restrictive, and two indicators may be used, out of the three indicators of the muscle strength, the balance, and the muscle mass, to calculate the MF.

Further, the height, body weight, gender, age and the like may be added as variables, in addition to the three indicators of the muscle strength, the balance, and the muscle mass, to calculate the overall motor function indicator MF.

Further, the example of displaying the three indicators of the muscle strength, the balance, and the muscle mass in the graph is shown in FIGS. 10A and 10B, but this is not restrictive. Stamina, agility, and flexibility that are measured separately may be inputted in advance via the operating switches 23 in FIG. 2, and evaluation values of the stamina, the agility, and the flexibility may be displayed together with the three indicators of the muscle strength, the balance, and the muscle mass that are measured by the motor function evaluation device 1 of this embodiment, so as to display further detailed advice. In this case, the graph becomes a radar chart having a rectangular shape to a hexagonal shape. By inputting a medical history, experiences of the falling, and status on daily activities in advance, more accurate advice can be given by taking them into consideration.

According to this embodiment, the muscle strength, the balance, and the muscle mass are determined from the measured load change and biological impedance in a time series by the CPU 24. However, the present invention is not limited thereto, and the measured load change and biological impedance in a time series may be outputted from the output port 22 to the external PC, and final calculation may be performed in the PC.

As described thus far, quantitative motor function evaluation can be made according to this embodiment.

The overall motor function indicator MF calculated in the present invention is the result of the measurement by the measuring device, which does not have a qualitative element such as comprehensive judgment of the survey and the results of the respective physical performance tests. Therefore, the overall motor function indicator MF is objective and has high reproducibility and reliability.

Further, as the indicator itself is determined in a comprehensive manner by at least two of the muscle strength, the balance ability, and the muscle mass, the reliability is higher than the case where the evaluation is made with one indicator.

Further, according to this embodiment, the evaluation of the overall motor function can be made simply, without performing the survey, the respective physical performance tests and the like. Further, as the evaluation can be made with one measuring device, it is possible to realize time saving, space saving, cost reduction and the like.

According to the measurement of the present invention, the subject stands still after the standing up motion from the chair, and keeps the standing position for several tens of seconds. This is one of the daily activities and can be performed with ease and within a short period of time. For this reason, opportunities of the measurement can be provided to various kinds of people and the measurement can be made with high frequency, which makes it possible to capture changes over time, that is the most important thing.

What is claimed is:

1. A motor function evaluation device comprising:
   a measurement base;
   a load measurement circuit configured to measure load change over time of a subject applied to the measurement base; and
   an arithmetic circuit configured to determine a balance ability indicator of the subject determined by the load change over time measured by the load measurement circuit, wherein:
   the arithmetic circuit is configured to determine the balance ability indicator based on a stabilizing time period, within which variation of the load measured by the load measurement circuit is stabilized, and
   the stabilizing time period is measured from a time when the subject stands up from a sitting position on a chair and the load applied to the load measurement circuit becomes a maximum value until a time when the variation of the load is stabilized.

2. The motor function evaluation device according to claim 1,
   wherein the arithmetic circuit is configured to determine a muscle strength indicator based on the maximum value and a weight of the subject.

3. A motor function evaluation method, comprising steps of:
   measuring load change over time of a subject applied to a measurement base;
   determining a balance ability indicator of the subject determined by the measured load change over time; and
   evaluating a motor function of the subject by using the balance ability indicator, wherein:
   the balance ability indicator is determined based on a stabilizing time period, within which variation of the load measured is stabilized, and
   the stabilizing time period is measured from a time when the subject stands up from a sitting position on a chair and the load applied to the measurement base becomes a maximum value until a time when variation of the load is stabilized.

4. The motor function evaluation device according to claim 1,
wherein the standing up motion of the subject is accompanied by an inclination of a back of the subject.

5. The motor function evaluation device according to claim 1,
wherein the time when the variation of the load is stabilized is defined as a time after a lapse of two cycles or a time when the load measured by the load measurement circuit has a same values as a body weight value after the lapse of the two cycles, after when the load applied to the load measurement circuit becomes the maximum value.

6. The motor function evaluation method according to claim 3,
wherein the time when the variation of the load is stabilized is defined as a time after a lapse of two cycles or a time when the load measured by the load measurement circuit has a same values as a body weight value after the lapse of the two cycles, after when the load applied to the load measurement circuit becomes the maximum value.

* * * * *